US008692010B1

(12) United States Patent
Korolev et al.

(10) Patent No.: US 8,692,010 B1
(45) Date of Patent: Apr. 8, 2014

(54) SYNTHESIS METHOD FOR COPPER COMPOUNDS

(75) Inventors: Andrey V. Korolev, Germantown, WI (US); Venkateswara R. Pallem, Hockessin, DE (US)

(73) Assignee: American Air Liquide, Inc., Fremont, CA (US)

( * ) Notice: Subject to any disclaimer, the term of this patent is extended or adjusted under 35 U.S.C. 154(b) by 67 days.

(21) Appl. No.: 13/549,067

(22) Filed: Jul. 13, 2012

(51) Int. Cl.
*C07F 1/08* (2006.01)

(52) U.S. Cl.
USPC .......................................... 556/110; 556/117

(58) Field of Classification Search
USPC ................................................ 556/110, 117
See application file for complete search history.

(56) References Cited

U.S. PATENT DOCUMENTS

| | | | |
|---|---|---|---|
| 3,594,216 | A | 7/1971 | Charles et al. |
| 6,620,956 | B2 | 9/2003 | Chen et al. |
| 7,087,774 | B2 | 8/2006 | Bradley et al. |
| 7,268,365 | B2 | 9/2007 | Bradley et al. |
| 2005/0003075 | A1 | 1/2005 | Bradley et al. |
| 2005/0107283 | A1 | 5/2005 | Bradley et al. |
| 2005/0267305 | A1 | 12/2005 | Bradley et al. |
| 2006/0141155 | A1 | 6/2006 | Gordon et al. |
| 2008/0044687 | A1 | 2/2008 | Bradley et al. |
| 2008/0171890 | A1 | 7/2008 | Kim et al. |
| 2008/0242880 | A1 | 10/2008 | Chen et al. |
| 2009/0042041 | A1 | 2/2009 | Grushin |
| 2010/0301478 | A1 | 12/2010 | Waichtler et al. |

FOREIGN PATENT DOCUMENTS

| | | |
|---|---|---|
| DE | 10 2007 058571 | 6/2009 |
| EP | 2 065 364 | 6/2009 |
| WO | WO 03 044242 | 5/2003 |
| WO | WO 2010 071364 | 6/2010 |
| WO | WO 2011 006035 | 1/2011 |

OTHER PUBLICATIONS

Aaltonen, T. et al., "Atomic layer deposition of noble metals—exploration of the low limit of the deposition temperature," Journal of Material Research, vol. 19, No. 11, Nov. 2004, pp. 3353-3358.
Basato, M. et al., "Coordinating properties of the anionic ligand (MeCO)2C(−)C(X)Me (X=O or NH)," Inorganica Chimica Acta 362 (2009), pp. 2551-2555.
Becht, M. et al., "Nickel thin films grown by MOCVD using Ni(dmg)$_2$ as precursor," Journal de Physique IV, Colloque C5, Supplement to Journal de Physique II, vol. 5, Jun. 1995, pp. C5-465 to C5-472.
Doppelt, P., "Why is coordination chemistry stretching the limits of micro-electronics technology?," Coordination Chemistry Reviews 178-180 (1998) pp. 1785-1809.
Everett, G.W. et al., "Existence of the planar [UNK] tetrahedral equilibrium in solutions of cobalt(II) complexes," J. Am. Chem. Soc., 1965, 87 (22), pp. 5266-5267.

Everett, G.W. et al., "The synthesis and proton resonance study of the solution equilibria of bis(β-ketoamino) nickel(II) complexes," Journal of the American Chemical Society (1965), 87(10), pp. 2117-2127.
Han, B. et al., "Atomic layer deposition of copper thin film using Cu$^{II}$(diketoiminate)$_2$ and H$_2$," Interconnect Technology Conference, 2009, IITC 2009, IEEE International, Jun. 2009, pp. 173-174.
Hitchcock, P.B. et al., "Synthesis and structures of the transition metal(II) β-diketiminates [ML$_2$] (M=Mn, Fe, Ni, Cu, Pd), [ML'2[ (M=Ni, Cu) and [M(η$^3$—C$_3$H$_5$)L] (M=Ni, Pd); L or L'=[{N(SiMe$_3$ or H)C(Ph)}$_2$CH]," Journal of Organometallic Chemistry, 2009, vol. 694, pp. 667-676.
Holme, T.P. et al., "Atomic layer deposition and chemical vapor deposition precursors selection method application to strontium and barium precursors," Journal of Physical Chemistry A, published on the internet Jul. 27, 2007, pp. A-E.
Huo, J. et al., "Characteristics of copper films produced via atomic layer deposition," Journal of Material Research, vol. 17, No. 9, Sep. 2002, pp. 2394-2398.
Liu, Y-H et al., "Synthesis and characterization of fluorinated β-ketoiminate and imino-alcohate Pd complexes—precursors for palladium chemical vapor deposition," Journal of Materials Chemistry, 2003, 13, opp. 135-142.
Mao, J. et al., "Scaling of copper seed layer thickness using plasma-enhanced ALD and an optimized precursor," Proceedings of the IEEE/SEMI Advanced Semiconductor Manufacturing Conference, Saratoga Springs, New York, New York, May 15-18, 2011.
Mao, J. et al., "Ultra-low temperature deposition of copper seed layers by PEALD" Abstract, Proceedings of the 218th ECS Meeting, Las Vegas, Nevada, Oct. 10-15, 2010.
Martensson, P. et al., "Atomic layer epitaxy of copper: Growth and selectivity in the Cu(II)-2,2,6,6-tetramethyl-3,5-heptanedionate/H$_2$ Process," Journal of the Electrochemical Society, vol. 145, No. 8, Aug. 1998, pp. 2926-2931.
Martensson, P. et al., "Use of atomic layer epitaxy for fabrication of Si—TiN—Cu structures," Journal of Vacuum Science and Technology B, 17(5), Sep./Oct. 1999, pp. 2122-2128.
Norman, J.A.T. et al., "New precursors for CVD copper metallization," Microelectronic Engineering 85 (2008), pp. 2159-2163.
Osowole, A.A. et al., "Synthesis and characterisation of some nickel(II) beta-ketoamines and their adducts with 2,2' bipyridine and 1/10-phenanthroline," Synthesis and Reactivity in Inorganic and Metal-Organic Chemistry (2002), 32(4), 783-799.
Park, K.-H. et al., 'Remarkably volatile copper(II) complexes of N,N2-unsymmetrically substituted 1,3-diketimines as precursors for Cu metal deposition via CVD or ALD, Journal of the American Chemical Society 2005, 127, pp. 9330-9331.
Park, J.W. et al., "Synthesis of Cu(II) aminoalkoxide complexes and their unusual thermolysis to Cu(0)," Inorganic Chemistry Communications 7 (2004), pp. 463-466.
Senocq, F. et al., "Thermal behaviour of CpCuPEt3 in gas phase and Cu thin films processing," Surface & Coatings Technology 201 (2007), pp. 9131-9134.

(Continued)

*Primary Examiner* — Porfirio Nazario Gonzalez
(74) *Attorney, Agent, or Firm* — Patricia E. McQueeney

(57) ABSTRACT

Disclosed are synthesis methods to produce copper bis-ketoiminate and copper bis-ketiminate compounds.

12 Claims, No Drawings

(56) References Cited

OTHER PUBLICATIONS

Solanki, R. et al., "Atomic layer deposition of copper seed layers," Electrochemical and Solid-State Letters, 3 (10) 2000, pp. 479-480.

Stabnikov, P.A. et al., "Saturated vapor pressure and crystal structure of bis-(2-imino-4-pentanonato)copper(II)," Journal of Structural Chemistry, 2003, vol. 44, No. 6, pp. 1054-1061.

Utriainen, M. et al., "Studies of NiO thin film formation by atomic layer epitaxy," Materials Science and Engineering B54 (1998) pp. 98-103.

Wu, L. et al., "Effects of hydrogen plasma treatments on the atomic layer deposition of copper," Electrochemical and Solid-State Letters (2008), 11(5), pp. H107-H110.

Wu, L. et al., "Hydrogen plasma-enhanced atomic layer deposition of copper thin films," Journal of Vacuum Science and Technology, Part B, vol. 25, No. 6, Dec. 11, 2007, pp. 2581-2585.

Yoshida, E. et al., "Palladium(II) complexes of beta-ketoamines eerived from acetylacetone and amines," Bulletin of the Chemical Society of Japan (1965), 38(12), pp. 2179-2182.

Zharkova, G.I. et al., "New volatile complexes of Ni(II) and Pd(II) with 2,2,6,6-tetramethyul-3-amino-4-hepten-5-one—structure and properties," Journal of Structural Chemistry, 2008, vol. 49, No. 2, pp. 309-316.

Zharkova, G.I. et al., "Synthesis, properties and crystal structures of volatile beta-ketomiminate Pd complexes, precursors for palladium chemical vapor deposition," Polyhedron 28 (2009), pp. 2307-2312.

International Search Report and Written Opinion for related PCT/US2010/041518, Oct. 7, 2010.

International Search Report and Written Opinion for related PCT/US2010/041471, Feb. 10, 2011.

SYNTHESIS METHOD FOR COPPER COMPOUNDS

TECHNICAL FIELD

Disclosed are synthesis methods to produce copper bis-ketoiminate and copper bis-diketiminate compounds.

BACKGROUND

Copper is becoming the preferred metal for interconnections, replacing aluminum and tungsten as conducting material due to its low resistivity (1.67 μΩcm for Cu, 2.65 μΩcm for Al), high electromigration resistance, and high melting point (1083° C. for Cu, 660° C. for Al). Its low interconnect resistivity may also result in faster devices.

Copper is usually electroplated inside trenches and holes in insulators; however before the electroplating step a thin continuous copper seed layer is needed. In the past sputtering techniques were used to deposit the seed layer, however due to demand for highly conformal and uniform films inside the trenches with high aspect ratios CVD- or ALD-type processes become necessary.

Several classes of Cu compounds including copper (II) bis-diketonates, copper (I) diketonate-olefin compounds, copper (I) amidinates, copper (II) aminoalkoxides, and copper (I) cyclopentadienyl complexes have been tried in CVD and ALD-type processes over the past decades. Recently, Air Liquide demonstrated excellent Cu seed layer depositions by PEALD process using copper (II) bis-ketoiminate compounds (see WO2011/006035).

The copper bis-ketoiminate compounds may be prepared either by reacting $CuCl_2$ or $CuBr_2$ with two equivalents of the lithium salt of the R-ketoimine ligand in tetrahydrofuran. The lithium salt reaction is shown as follows:

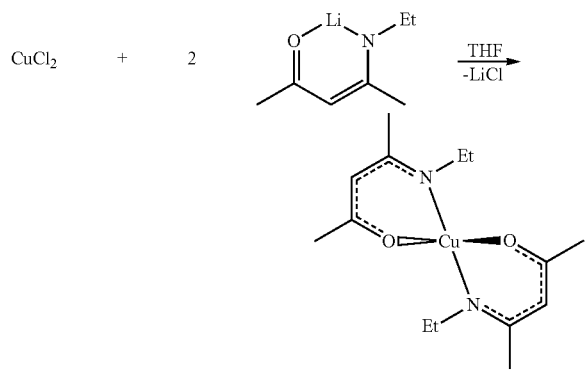

As shown in the comparative examples that follow, initial testing by Applicants resulted in no yield. Optimization of the method may result in some yield, but it would most likely be low.

The copper bis-ketoiminate compounds may also be prepared as described in the literature (see, e.g., P. A. Stabnikov, J. Structural Chemistry 2003, 44, 6, 1054-1061) by reacting copper acetate $(Cu(OAc)_2)$ with the R-ketoimine in aqueous alcohol in the presence of excess ammonia.

Bradley et al. disclose the synthesis of copper bis-diketiminate compounds in Example 4 of US Pat. App. Pub. No. 2008/0044687, which is summarized below.

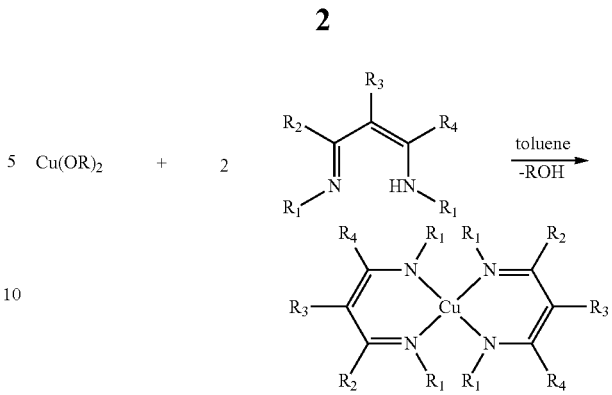

Chen et al. disclose the synthesis of copper bis-diketiminate compounds in the hypothetical example of U.S. Pat. No. 6,620,956 by reacting $CuCl_2$ with two molar equivalents of the lithium salt of the R-ketoimine in diethyl ether.

A need remains for improved synthesis methods for the copper bis-ketoiminate and copper bis-diketiminate compounds.

NOTATION AND NOMENCLATURE

Certain abbreviations, symbols, and terms are used throughout the following description and claims, and include:

As used herein, the indefinite article "a" or "an" means one or more.

As used herein, the term "immediately" means without delay.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, pentyl groups, etc. Examples of branched alkyls groups include without limitation t-butyl. Examples of cyclic alkyl groups include without limitation, cyclopropyl groups, cyclopentyl groups, cyclohexyl groups, etc.

As used herein, the abbreviation "Me" refers to a methyl group; the abbreviation "Et" refers to an ethyl group; the abbreviation "Pr" refers to a n-propyl group; the abbreviation "iPr" refers to an isopropyl group; the abbreviation "nBu" refers to n-butyl, the abbreviation "tBu" refers to a tert-butyl; and the abbreviation "sBu" refers to a sec-butyl.

The standard abbreviations of the elements from the periodic table of elements are used herein. It should be understood that elements may be referred to by these abbreviations (e.g., Cu refers to copper, N refers to nitrogen, C refers to carbon, etc.).

SUMMARY

Disclosed are methods of synthesizing a copper bis-diketiminate compound having the formula of Compound (I) or a copper bis-ketoiminate compound having the formula of Compound (II):

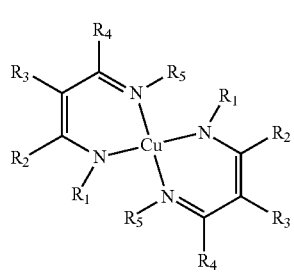

Compound (I)

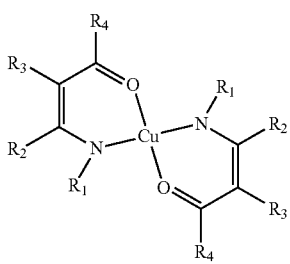

Compound (II)

wherein each of $R_1$ to $R_5$ is independently selected from the group consisting of H, C1-C5 alkyl, alkyl amino, and $SiR'_3$, wherein R' is a C1-C5 alkyl. A copper halide is dissolved in a first anhydrous solvent to produce a copper halide solution. A solution of a sodium alkoxide in a second anhydrous solvent is mixed with the copper halide solution to produce a suspension. A solution of a diketimine or a ketoimine in a third anhydrous solvent is added to the suspension to produce a final mixture. The copper bis-diketiminate compound or the copper bis-ketoiminate compound is isolated from the final mixture. The disclosed methods may further include one or more of the following aspects:

- the step of mixing the copper halide solution with the solution of sodium alkoxide in the anhydrous solvent is performed for approximately 30 minutes to approximately 90 minutes;
- the solution of the diketimine or the ketoimine is immediately added to the suspension;
- the solution of the diketimine or the ketoimine is added to the suspension after the mixture is stirred for approximately one hour;
- the copper halide is $CuCl_2$;
- the sodium alkoxide is sodium methoxide;
- the diketimine is N,N'-diethyl-diketimine;
- the ketoimine is N-ethyl-ketoimine;
- purifying the copper bis-diketiminate or the copper bis-ketoiminate compound;
- each of the first anhydrous solvent and the second anhydrous solvent is independently selected from the group consisting of methanol, ethanol, and isopropanol;
- the third anhydrous solvent is selected from the group consisting of methanol, ethanol, isopropanol, toluene, and tetrahydrofuran; and
- each of the first anhydrous solvent, the second anhydrous solvent, and the third anhydrous solvent is methanol.

DETAILED DESCRIPTION OF PREFERRED EMBODIMENTS

Disclosed are methods of synthesizing copper bis-diketiminate compounds having the formula of Compound (I) or copper bis-ketoiminate compounds having the formula of Compound (II):

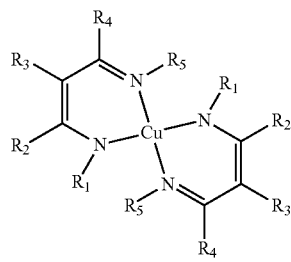

Compound (I)

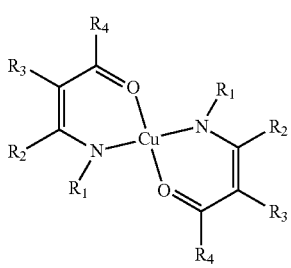

Compound (II)

wherein each of $R_1$ to $R_5$ is independently selected from the group consisting of H, C1-C5 alkyl, alkyl amino, and $SiR'_3$, wherein R' is a C1-C5 alkyl.

Exemplary bis-diketiminate copper compounds include
bis(4-amino-3-penten-2-iminato)Copper(II),
bis(4-N-methylamino-3-penten-2-N-methyliminato)Copper(II),
bis(4-N-ethylamino-3-penten-2-N-ethyliminato)Copper(II),
bis(4-N-isopropylamino-3-penten-2-N-isopropyliminato)Copper(II),
bis(4-N-n-propylamino-3-penten-2-N-n-propyliminato)Copper(II),
bis(4-N-n-butylamino-3-penten-2-N-n-butyliminato)Copper(II),
bis(4-N-isobutylamino-3-penten-2-N-isobutyliminato)Copper(II),
bis(4-N-sec-butylamino-3-penten-2-N-sec-butyliminato)Copper(II), and
bis(4-N-tert-butylamino-3-penten-2-N-tert-butyliminato)Copper(II).

Exemplary bis-ketoiminate copper compounds include
bis(4N-(amino)pent-3-en-2-onato)Copper(II),
bis(4N-(methylamino)pent-3-en-2-onato)Copper(II),
bis(4N-(ethylamino)pent-3-en-2-onato)Copper(II),
bis(4N-(isopropylamino)pent-3-en-2-onato)Copper(II),
bis(4N-(n-propylamino)pent-3-en-2-onato)Copper(II),
bis(4N-(n-butylamino)pent-3-en-2-onato)Copper(II),
bis(4N-(isobutylamino)pent-3-en-2-onato)Copper(II),
bis(4N-(secbutylamino)pent-3-en-2-onato)Copper(II), and
bis(4N-(tertbutylamino)pent-3-en-2-onato)Copper(II).

The copper bis-diketiminate compounds and the copper bis-ketoiminate compounds are synthesized by dissolving a copper halide in a first anhydrous solvent to produce a copper halide mixture. Suitable copper halides include $CuCl_2$, $CuBr_2$, $CuI_2$, or mixtures thereof. The first anhydrous solvent may be an alcohol, such as methanol, ethanol, or isopropanol. The copper halide dissolves readily in the alcohol.

A solution of a sodium alkoxide in a second anhydrous solvent is added to and mixed with the copper halide solution to produce a suspension. Suitable sodium alkoxides include sodium methoxide, sodium ethoxide, sodium n-propoxide, and sodium isopropoxide. The second anhydrous solvent may be an alcohol, such as methanol, ethanol, or isopropanol. The second anhydrous solvent may be the same as the first anhydrous solvent used to dissolve the copper halide. The sodium alkoxide dissolves in the second anhydrous solvent.

The sodium alkoxide solution may be added to the copper halide solution using a stainless steel cannula or any other non-reactive transfer device that prevents exposure of the solutions to air. The sodium alkoxide and copper halide solutions may be mixed together for approximately 5 to approximately 60 minutes. The addition may occur at cool to room temperature (approximately 0° C. to approximately 30° C.). The sodium alkoxide and copper halide react to form precipitates of sodium halide and copper alkoxide suspended in the solution.

A solution of a diketimine or a ketoimine in a third anhydrous solvent is added to the suspension to produce a final mixture. The diketimine or ketoimine may be produced by methods well known in the art (see, e.g., Examples 1 and 4 that follow). The third anhydrous solvent may be selected from methanol, ethanol, isopropanol, toluene, or tetrahydrofuran (THF). The third anhydrous solvent may be the same as the first anhydrous solvent and/or the second anhydrous solvent. The diketimine/ketoimine solution may be added to the suspension using a stainless steel cannula or any other non-reactive transfer device that prevents exposure of the solutions to air. The diketimine/ketoimine solution and the suspension may be mixed for approximately 12 to approximately 48 hours at approximately room temperature (approximately 20° C. to approximately 30° C.).

The diketimine/ketoimine solution is preferably added immediately to the suspension after mixing the suspension for approximately 5 to approximately 60 minutes. Better yields are obtained when the diketimine/ketoimine solution is added immediately to the freshly prepared suspension of the sodium alkoxide solution and copper halide. Aging of the suspension results in longer reaction times and moderate to very low yields of the copper bis-diketimine and copper bis-ketoimine compounds, along with production of viscous by-products that are insoluble in the anhydrous solvents.

The copper bis-diketiminate compounds or the copper bis-ketoiminate compounds are isolated from the final mixture. Standard isolation techniques known in the art may be utilized, such as removal of the solvents, mixing with nonpolar solvents such as pentane and filtering the mixture, and the like. The yields before purification are essentially quantitative.

The isolated copper bis-diketiminate compounds or the copper bis-ketoiminate compounds may be purified by techniques known in the art, such as distillation (for liquid products) or sublimation (for solid products). Applicants consistently obtained final purified yields of greater than 50% w/w yield, and a large number of final purified yields greater than 75% w/w.

The disclosed synthesis methods generate $Cu(OR)_2$ in situ (from copper halide and sodium methoxide). The freshly produced $Cu(OR)_2$ reacts with the diketimine or ketoimine to produce the target products fast (within approximately 24 hours). Applicants believe that isolation of $Cu(OR)_2$ reduces its reactivity, resulting in longer reaction times and lower yields. Additionally, the sodium halide by-products do not affect the reaction pathway. The sodium halide by-products are easily separated from the copper bis diketiminate and copper bis ketoiminate products by filtration. Furthermore, by generating the $Cu(OR)_2$ in situ, the synthesis method may be performed in one vessel (i.e., a "one pot" method), reducing equipment requirements and synthesis time. Finally, the purchase of copper halide and sodium alkoxide to generate $Cu(OR)_2$ is currently less expensive than the purchase of $Cu(OR)_2$.

The disclosed synthesis methods significantly reduce reaction times as compared to the prior art methods. The disclosed synthesis methods provide quick and easy product separation from by-products and the reaction mixture. Finally, the disclosed synthesis methods provide consistently high yields of the product.

EXAMPLES

The following examples illustrate experiments performed in conjunction with the disclosure herein. The examples are not intended to be all inclusive and are not intended to limit the scope of disclosure described herein.

All synthesis methods were performed under an air free atmosphere and all solvents were purified and dried.

Example 1

Synthesis of Ketoimine 2,4-pentanedione (119.4 g, 1.19 mol) was mixed with 200 mL of anhydrous methanol and 40 g of anhydrous sodium sulfate in a 2 L Schlenk flask. Ethylamine (620 mL of 2.0 M solution in MeOH, 1.24 mol) was added dropwise to the reaction mixture using addition funnel. A slightly exothermic reaction occurred, and the solution gained yellow color. The mixture was stirred at room temperature overnight and filtered through the fritted glass filter. Solvent was removed from the yellow filtrate under reduced pressure (using the rotavap) leaving a yellow liquid. The crude product was distilled using a 1' Vigreux column; the main fraction boiled at 43-45° C./80 mTorr. 147 g (97% yield) of a colorless liquid was obtained.

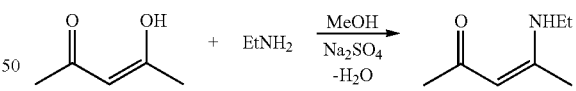

$^1$H NMR ($C_6D_6$): δ 11.01 (br.s, 1H, NH), 4.86 (s, 1H, CH), 2.59 (m, 2H, $CH_3CH_2N$), 2.00 (s, 3H, $CH_3CO$), 1.41 (s, 3H, $CH_3CN$), 0.71 (t, 3H, $CH_3CH_2N$)

Example 2

Synthesis of Copper (II) bis(N-isopropyl-ketoiminate) Compounds $CuCl_2$ (6.0 g, 44.6 mmol) was dissolved in 50 mL of anhydrous methanol in a 250 mL Schlenk flask producing a bright green solution. NaOMe (4.82 g, 89.3 mmol) was dissolved in 50 mL of anhydrous methanol in a 100 mL Schlenk flask, and the colorless solution was added to the $CuCl_2$ solution via stainless steel canula at room temperature. A bright green precipitate formed initially and quickly converted to a very dark blue precipitate of Cu(OMe)$_2$. The mixture was stirred at room temperature for 1 h. N-isopropyl-ketoimine prepared in a manner similar to that of Example 1 (12.6 g, 89.3 mmol) was added to the Cu(OMe)$_2$ suspension via stainless steel canula. No reaction occurred after 3 days of stirring at room temperature. Methanol was distilled off at atmospheric pressure, and toluene (100 mL) was added to the dark red residue. The mixture was stirred at 100° C.-110° C. for 5 hours and cooled to room temperature. The mixture was filtered through a filter medium. The solids on the filter medium were washed with 3×20 mL of pentane. The solvents were removed from the filtrate under vacuum leaving a dark red solid residue. The crude material was sublimated at 120° C./10 mtorr. 8.7 g (57% yield) of the dark red solid product was obtained. Applicants believe that reactions utilizing the larger isopropyl substituent on the ketominate require more energy and produce lower yields as compared to reactions utilizing the smaller ethyl substituent in Example 3 below. However, only one isopropyl-ketoiminate compound has been synthesized to date.

Example 3

Synthesis of Copper (II) bis(N-ethyl-ketoiminate) Compounds

CuCl$_2$ (17.8 g, 0.132 mol) was dissolved in 100 mL of anhydrous methanol. To this solution was added a solution of NaOMe (14.3 g, 0.265 mol) in 200 mL of anhydrous methanol. The mixture was stirred for 1 h at room temperature, and a dark blue suspension formed. N-ethyl-ketoimine prepared in a manner similar to that of Example 1 (33.7 g, 0.265 mol) was added to this suspension via cannula. A dark yellow-green mixture formed, it was stirred at room temperature for 24 h. Methanol was removed from the reaction mixture under vacuum, and the residue was mixed with 200 mL of pentane. The mixture was stirred and filtered through a filter medium. The solids on the filter medium were washed with 3×10 mL of pentane. Pentane was removed from the dark yellow-green filtrate under vacuum leaving a dark yellow-green viscous liquid which was distilled under 110-115° C./40-55 mtorr to give 41.4 g (99% yield) of the dark yellow-green liquid.

Example 4

Synthesis of Diketimine

Ethyl-enaminoketone (137.5 g, 1.08 mol) was mixed with 100 mL of dichloromethane and dimethylsulfate (102.2 mL, 1.08 mol). The mixture was stirred at 40° C. for 24 h and at room temperature for 40 h. Ethylamine (600 mL of 2.0 M solution in THF, 1.2 mol) was added, and the mixture was stirred at room temperature overnight. Solvents were removed under vacuum leaving a very viscous red oil. NaOMe (58.34 g, 1.08 mol) was dissolved in methanol (400 mL), and the solution was added to the reaction mixture residue. A red solution with white precipitate formed. The mixture was stirred at room temperature overnight. Methanol was removed under vacuum, and 500 mL of pentane was added to the residue. The mixture was stirred for 30 min, and filtered through the fritted glass filter. The solids on the filter were washed with 3×100 mL of pentane. Pentane was removed from the red filtrate on the rotavap leaving a dark red liquid residue. It was fractionally distilled using a 6" Vigreux column; the main fraction boiled at 35-37° C./150 mTorr. 134.1 g (80.5% yield) of a light yellow liquid that crystallized at 20° C. was obtained.

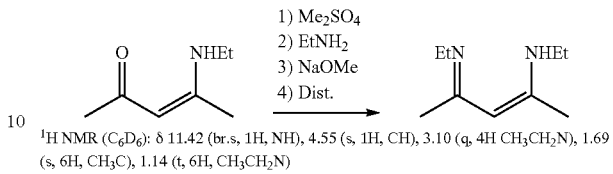

$^1$H NMR (C$_6$D$_6$): δ 11.42 (br.s, 1H, NH), 4.55 (s, 1H, CH), 3.10 (q, 4H CH$_3$CH$_2$N), 1.69 (s, 6H, CH$_3$C), 1.14 (t, 6H, CH$_3$CH$_2$N)

Example 5

Synthesis of Copper (II) bis(N,N'-diethyl-diketiminate) Compounds

CuCl$_2$ (4.47 g, 33.2 mmol) was dissolved in 20 mL of anhydrous MeOH in a 100 mL Schlenk flask producing a bright green solution. NaOMe (3.60 g, 66.6 mmol) was dissolved in 20 mL of anhydrous MeOH in a 100 mL Schlenk flask, and the colorless solution was added to the CuCl$_2$ solution via stainless steel canula at room temperature. A bright green precipitate formed initially and quickly converted to a very dark blue precipitate of Cu(OMe)$_2$. The mixture was stirred at room temperature for 1 hour. N,N' diethyl-diketimine (10.4 g, 66.6 mmol) was added to the Cu(OMe)$_2$ suspension via stainless steel canula. The N,N'-diethyl-diketimine was prepared in a manner similar to that of Example 4. The mixture immediately turned dark purple. It was stirred at room temperature for 2 days. MeOH was removed from the reaction mixture under vacuum, and the dark purple residue was kept at 80° C. under vacuum for 5 h to remove unreacted ligand. The remaining solid was sublimed at 90-110° C./20-40 mtorr. 7.5 g (61% yield) of a very dark purple crystalline material was obtained. The diketiminate compounds appear to produce lower yields when compared to the ketoiminate compounds.

Example 6

Synthesis of Copper (II) bis(N,N'-diethyl-diketiminate) Compounds

CuCl$_2$ (8.4 g, 0.062 mol) was dissolved in 50 mL of anhydrous methanol. To this solution was added a solution of NaOMe (6.7 g, 0.124 mol) in 100 mL of anhydrous methanol. The mixture was stirred for 1 hour at room temperature, and a dark blue suspension formed. A solution of N,N'-diethyl-diketimine (19.2 g, 0.124 mol) in 50 mL of anhydrous methanol was added to this suspension via cannula. The N,N'-diethyl-diketimine was prepared in a manner similar to that of Example 4. A dark purple mixture formed, it was stirred at room temperature for 24 hours. Methanol was removed from the reaction mixture under vacuum, and the residue was mixed with 100 mL of pentane. The mixture was stirred and filtered through a filter medium. The solids on the filter medium were washed with 3×10 mL of pentane. Pentane was removed from the dark purple filtrate under vacuum leaving a dark purple solid which sublimed under 90-110° C./40-50 mtorr to give 20 g (87% yield) of the dark purple crystalline solid.

Comparative Example 1

Synthesis of Cu (II) bis(N-ethyl-ketoiminate) Compounds

Applicants attempted to synthesize Cu (II) bis(N-ethyl-ketoiminate) according to the following method:

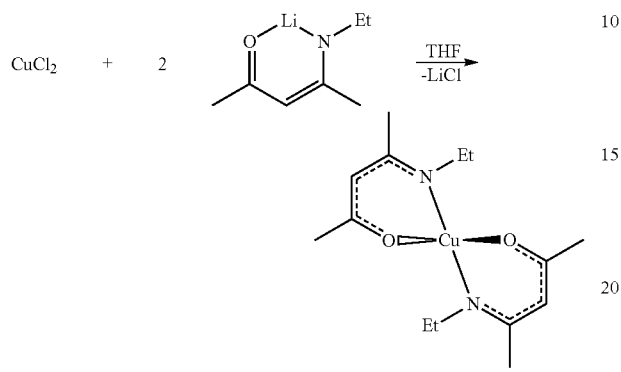

Initial testing by Applicants resulted in no yield. Optimization of the method may result in some yield, but it would most likely be low.

Comparative Example 2

Synthesis of Cu (II) bis(N-ethyl-ketoiminate) Compounds

Applicants synthesized copper bis-ketoiminate compounds by reacting commercially purchased copper acetate (Cu(OAc)$_2$) with R-ketoimine in THF or by reacting commercially purchased copper methoxide (Cu(OMe)$_2$) with R-ketoimine in alcohol or toluene. Initial testing in THF and ethanol resulted in no to negligible purified yields (max 2% w/w). Initial testing in toluene resulted in poor purified yields (<25% w/w). Initial testing in methanol results in moderate purified yields (53% w/w). Once again, optimization of the method may improve the yield results, but would most likely not produce results similar to those produced by the disclosed synthesis methods.

Comparative Example 3

Synthesis of Copper (II) bis(N,N'-diethyl-diketiminate) Compounds

Applicants synthesized copper bis-ketimate compounds by reacting commercially purchased copper methoxide (Cu(OMe)$_2$) with R-diketimine in methanol, THF, or ethanol. The reaction times were long (typically 2-3 days of stirring). Product isolation was difficult due to the presence of viscous brown by-products. Finally, yields were inconsistent, with the yields from analogous processes varying from 27% w/w to 60% w/w.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

We claim:

1. A method of synthesizing a copper bis-diketiminate compound having the formula of Compound (I) or a copper bis-ketoiminate compound having the formula of Compound (II):

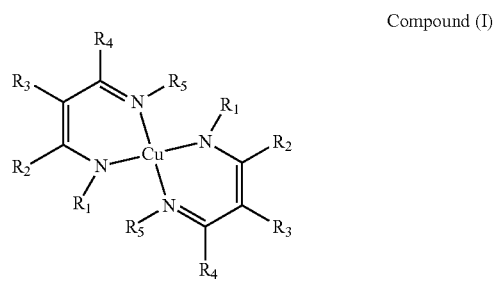

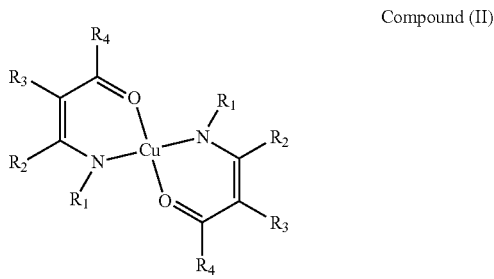

wherein each of $R_1$ to $R_5$ is independently selected from the group consisting of H, C1-C5 alkyl, alkyl amino, and SiR'$_3$, wherein R' is a C1-C5 alkyl, the method comprising:
   Dissolving a copper halide in a first anhydrous solvent to produce a copper halide solution,
   mixing the copper halide solution with a solution of a sodium alkoxide in a second anhydrous solvent to produce a suspension,
   adding to the suspension a solution of a diketimine or a ketoimine in a third anhydrous solvent to produce a final mixture, and
   isolating the copper bis-diketiminate compound or the copper bis-ketoiminate compound from the final mixture.

2. The method of claim 1, wherein the step of mixing the copper halide solution with the solution of sodium alkoxide in the anhydrous solution is performed for approximately 30 minutes to approximately 90 minutes.

3. The method of claim 1, wherein the solution of the diketimine or the ketoimine is immediately added to the suspension.

4. The method of claim 1, wherein the solution of the diketimine or the ketoimine is added to the suspension after the mixture is stirred for approximately one hour.

5. The method of claim 1, wherein the copper halide is CuCl$_2$.

6. The method of claim 1, wherein the sodium alkoxide is sodium methoxide.

7. The method of claim 1, wherein the diketimine is N,N'-diethyl-diketimine.

8. The method of claim 1, wherein the ketoimine is N-ethyl-ketoimine.

9. The method of claim 1, further comprising purifying the copper bis-diketiminate or the copper bis-ketoiminate compound.

10. The method of claim 1, wherein each of the first anhydrous solvent and the second anhydrous solvent are independently selected from the group consisting of methanol, ethanol, and isopropanol.

11. The method of claim 1, wherein the third anhydrous solvent is selected from the group consisting of methanol, ethanol, isopropanol, toluene, and tetrahydrofuran.

12. The method of claim 1, wherein each of the first anhydrous solvent, the second anhydrous solvent, and the third anhydrous solvent is methanol.

\* \* \* \* \*